United States Patent [19]

Takarada et al.

[11] Patent Number: 5,525,462
[45] Date of Patent: Jun. 11, 1996

[54] NUCLEIC ACID SEQUENCE AMPLIFICATION METHOD, DETECTION METHOD, AND REAGENT KIT THEREFOR

[75] Inventors: Yutaka Takarada; Toshiya Aono; Shuji Shibata, all of Ohtsu, Japan

[73] Assignee: Toyo Boseki Kabushiki Kaisha, Osaka, Japan

[21] Appl. No.: 875,758

[22] Filed: Apr. 28, 1992

[30] Foreign Application Priority Data

May 2, 1991 [JP] Japan ................................. 3-130360
Nov. 1, 1991 [JP] Japan ................................. 3-315483

[51] Int. Cl.$^6$ .......................... C12Q 1/68; C12P 19/34; C07H 21/04
[52] U.S. Cl. ......................... 435/6; 435/91.1; 435/91.2; 536/24.33
[58] Field of Search ..................... 435/91, 6, 810; 536/27

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,994,368 | 2/1991 | Goodman et al. | 435/6 |

FOREIGN PATENT DOCUMENTS

0469755A1 7/1991 European Pat. Off.
0549107A1 10/1992 European Pat. Off.

OTHER PUBLICATIONS

Kwok et al., *Nature* 339, 237–238 (1989).
Nelson et al., *PNAS* 86, 6686–6690 (1989).
Frohman et al., *PNAS* 85, 8998–9002 (1988).
Wu and Wallace, *GENOMICS* 4, 560–569 (1989).
Sambrook et al., *Molecular Cloning*, Cold Spring Harbor Laboratory Press, see pp. 5.73–5.77 (1989).

*Primary Examiner*—Kenneth R. Horlick
*Attorney, Agent, or Firm*—Leydig, Voit & Mayer, Ltd.

[57] ABSTRACT

An oligonucleotide is provided, which has at least a base sequence A, which is 10–30 nucleotides in length and homologous to a part of a specific nucleic acid sequence to be amplified, and a base sequence B, which is 10–30 nucleotides in length and complementary to a sequence 3' to the part of the specific nucleic acid sequence to be amplified. Sequences A and B are separated by a spacer region of 0–20 nucleotides. The oligonucleotide is used in an amplification method, wherein the oligonucleotide is mixed with a sample containing a specific nucleic acid sequence to be amplified and allowed to anneal to the specific nucleic acid sequence in the sample. The annealed oligonucleotide acts as a primer in an elongation reaction, whereas any nonannealed oligonucleotide is decomposed, except for at least part of the base sequence A. The elongation product is then denatured to a single strand for use as a template to which the remaining oligonucleotide anneals to form a primer for subsequent elongation. Also provided is a detection method, which allows for detection of a specific nucleic acid sequence in a sample, as well as reagent kits for use in the amplification and detection methods.

18 Claims, 6 Drawing Sheets

NUCLEIC ACID SEQUENCE AMPLIFICATION METHOD, DETECTION METHOD, AND REAGENT KIT THEREFOR

FIELD OF THE INVENTION

The present invention relates to a method for amplifying a specific nucleic acid sequence present in a sample and detecting same. More specifically, the present invention relates to a method for optionally producing a specific nucleic acid sequence from given nucleic acids in larger amounts as compared with the amount initially present therein. Said nucleic acid may be single-stranded or double-stranded, and may be in a relatively pure form or a component of a mixture.

BACKGROUND OF THE INVENTION

In recent years, it has become a common practice to detect nucleic acid sequences by hybridization as an efficient means of diagnosis of genetic diseases, cancer, infection, and other diseases.

The target base sequence is often only a very small portion of the detection subject nucleic acid; and when an oligonucleotide probe with an end labeled with a non-radioactive marker or an oligonucleotide probe labeled with a radioisotope is used, nucleic acid sequence detection is sometimes difficult due to insufficient sensitivity and other problems. Much effort has, therefore, been made to improve probe detection system sensitivity (W087/03622).

A published means of sensitivity improvement includes amplifying the target nucleic acid sequence to be detected with the use of DNA polymerase (Japanese Patent Unexamined Publication No. 274697/1986, hereinafter sometimes abbreviated as PCR). This method, however, requires frequent heating and cooling for repeated cycles of primer annealing, elongation and denaturation, which in turn demands specially designed equipment or much labor. Also, this method uses two oligonucleotides as primers. Amplification by DNA polymerase may occur even when these oligonucleotides have annealed nonspecifically, and stringent primer specificity is required.

Another published means is the amplification method using DNA ligase (W089/12696, Japanese Patent Unexamined Publication No. 2934/1990). This method, however, involves nonspecific amplification by DNA ligase blunt-end ligation. To avoid this phenomenon, the method using three or more sets of oligonucleotide probes has been published (W089/12696), but this method requires high cost because a large number of probes are necessary. Another published method uses a combination of DNA ligase and DNA polymerase (W090/01069). However, this method also poses a problem of high cost because it requires at least four oligonucleotides in two sets. Another method requires three oligonucleotides, two of which require several dozens of nucleotides, resulting again in high cost.

Also, it is a well-known fact that RNA is produced from DNA by the action of RNA polymerase, and a nucleic acid amplification method using RNA polymerase has been published (W089/01050). In this method, however, satisfactory amplification cannot be achieved solely by transcription and amplification with RNA polymerase. Therefore, the resulting RNA again undergoes the action of reverse transcriptase to produce DNA. Generally, transcription to DNA by reverse transcriptase is faulty, since it often accompanies reading errors in comparison with DNA replication by DNA polymerase. There is a known method in which only the probe which has correctly hybridized to the target nucleic acid is amplified [BIO/TECHNOLOGY vol. 6, 1197 (1988)]. This method, however, has a shortcoming in that the blank value increases because the probe bound by nonspecific reaction is also amplified.

SUMMARY OF THE INVENTION

An object of the present invention is to provide a simple and convenient method of target specific nucleic acid sequence amplification.

Another object of the present invention is to provide a method for detecting a specific nucleic acid sequence in a sample.

DETAILED DESCRIPTION OF THE INVENTION

Figure 1:
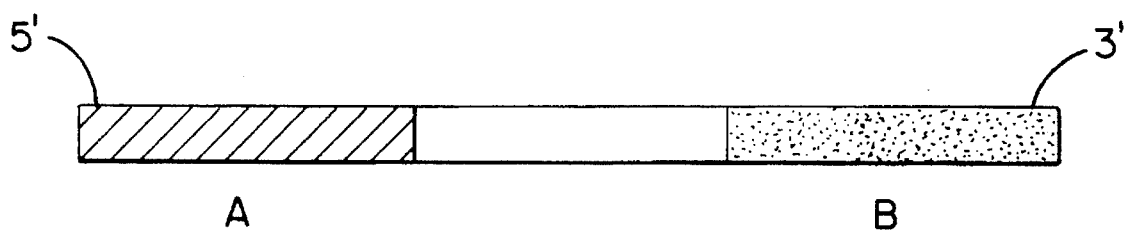
FIG. 1 shows an example of the oligonucleotide of the present invention wherein A is a base sequence homologous to a part of the specific nucleic acid sequence, and B is a base sequence complementary to the sequence at the 3' downstream position from said part of the specific nucleic acid sequence.
Figure 2:
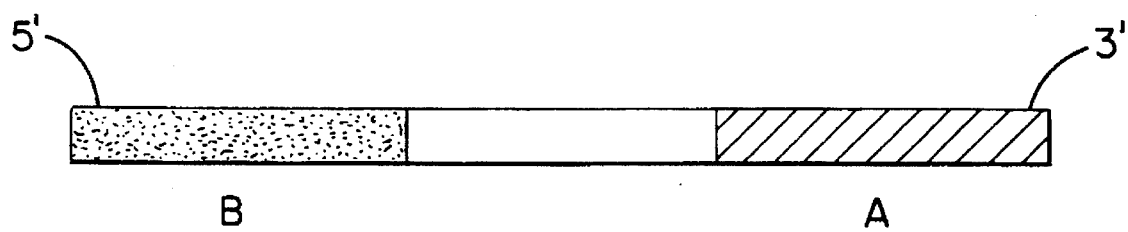
FIG. 2 shows an example of the oligonucleotide of the present invention, wherein A is a base sequence homologous to a part of the specific nucleic acid sequence, and B is a base sequence complementary to the sequence at the 5' upstream position from said part of the specific nucleic acid sequence.

With the aim of solving the problems described above, the present inventors have made intensive investigations, and found an oligonucleotide having at least a base sequence A and a base sequence B, wherein the base sequence A homologous to a part of the specific nucleic acid sequence or the base sequence B complementary thereto, and the base sequence B complementary to the sequence at the 3' downstream position from said part of the specific nucleic acid sequence or the base sequence A homologous thereto are present in sequential arrangement in the direction from the 5' terminal to the 3' terminal. Specifically, this oligonucleotide is one which has at least a base sequence A and a base sequence B, wherein the base sequence A homologous to a part of the specific nucleic acid sequence and the base sequence B complementary to the sequence at the 3' downstream position from said part of the specific nucleic acid sequence are present in sequential arrangement in the direction from the 5' terminal to the 3' terminal, or one which has a base sequence A and a base sequence B, wherein the base sequence B complementary to a part of the specific nucleic acid sequence and the base sequence A homologous to the sequence at the 3' downstream position from said part of the specific nucleic acid sequence are present in sequential arrangement in the direction from the 5' terminal to the 3' terminal. These oligonucleotides are shown in FIGS. 1 and 2.

The present inventors have also found that the problems can be solved by using an oligonucleotide having at least a base sequence A homologous to a part of the specific nucleic acid sequence and a base sequence B complementary to the sequence at the 3' downstream position from said part of the specific nucleic acid sequencer in sequential arrangement in the direction from the 5' terminal to the 3' terminal, which resulted in the completion of the present invention.

Accordingly, the present invention essentially comprises the following:

(1) A method for amplifying at least one specific nucleic acid sequence contained in a sample, which comprises the following procedures.

(a) An oligonucleotide having at least a base sequence A homologous to a part of the specific nucleic acid sequence and a base sequence B complementary to the sequence at the 3' downstream position from said part of the specific nucleic acid sequence in sequential arrangement in the direction from the 5' terminal to the 3' terminal is mixed with a sample, and allowed to react for annealing the specific nucleic acid sequence in the sample with the above-mentioned oligonucleotide.

(b) Using the annealed oligonucleotide as the primer, the elongation reaction is carried out.

(c) The unreacted oligonucleotide is decomposed, except for at least one part of the base sequence A homologous to a part of the specific nucleic acid sequence.

(d) The elongation product obtained in (b) is denatured to a single strand.

(e) Using this single strand obtained in (d) as the template, the oligonucleotide obtained in (c) is reacted as the primer to yield an elongation product.

(2) An amplification method comprising the following procedure (f) or (f') in addition to the above procedures (a) to (e).

(f) The elongation product obtained in (e) is denatured to a single strand. The oligonucleotide obtained in (c) is used as the primer to repeat synthesis of the elongation product at least once.

(f') The elongation product obtained in (e) is subjected to the procedures (a) to (e) at least once.

(3) An amplification method comprising the following procedures (f) and (g) in addition to the above procedures (a) to (e).

(f) The elongation product obtained in (e) is denatured to a single strand. The oligonucleotide obtained in (c) is used as the primer to repeat synthesis of the elongation product at least once.

(g) The amplification product obtained in (f) is subjected to the procedures (a) to (e) or (a) to (f) at least once.

The oligonucleotide of the present invention is designed to have at least a base sequence A homologous to a part of the specific nucleic acid sequence and a base sequence B complementary to the sequence at the 3' downstream position from said part of the specific nucleic acid sequence in sequential arrangement in the direction from the 5' terminal to the 3' terminal. The structure and length thereof are not particularly limited. Generally, the length of the base sequence A homologous to a part of the specific nucleic acid sequence and/or a base sequence B complementary to a part of the specific nucleic acid sequence is 6–100 nucleotides, preferably 10–30 nucleotides.

It is also possible to provide a spacer between the base sequence A homologous to a part of the specific nucleic acid sequence and the base sequence B complementary to the sequence other 3' downstream position from said part of the specific nucleic acid sequence when desired (FIG. 1). This spacer is generally 1–100, preferably 1–20 nucleotides in length.

Said oligonucleotide can be synthesized by the phosphoamidite method using a DNA synthesizer, such as the DNA synthesizer Model 391 (Applied Biosystems Inc.), and by any other method, such as the phosphotriester method, the H-phosphonate method, the thiophosphite method, and so on. Also, they may be isolated from a biological origin and are exemplified by a restriction endonuclease digestion product.

The reagent kit for the amplification of the target nucleic acid of the present invention contains the aforementioned oligonucleotide, nuclease, nucleic acid polymerase and/or reverse transcriptase, 4 kinds of deoxyribonucleotide triphosphate, and reaction buffer.

The method for detecting the nucleic acid sequence of the present invention involves the above-mentioned procedures (a), (b), (c), (d) and (e) or (a), (b), (c), (d), (e) and (f), or (a), (b), (c), (d), (e) and (f'), using a labeled oligonucleotide, and measuring the labeled marker for the detection of at least one specific nucleic acid sequence contained in a sample.

Further, the method for detecting the nucleic acid sequence of the present invention involves the above-mentioned procedures (a), (b), (c), (d) and (e) or (a), (b), (c), (d), (e) and (f), or (a), (b), (c), (d), (e) and (f'), adding a labeled oligonucleotide probe capable of hybridizing with the sequence to be detected in the product and/or its variant, and detecting the presence or absence of said hybridization for the detection of the target nucleic acid sequence.

The reagent kit for the detection of the target nucleic acid sequence of the present invention contains the aforementioned labeled oligonucleotide, nuclease, nucleic acid polymerase and/or reverse transcriptase, 4 kinds of deoxyribonucleotide triphosphate, a reaction buffer, and a marker detection system.

Further, the reagent kit for the detection of the target nucleic acid sequence of the present invention contains the aforementioned oligonucleotide, nuclease, nucleic acid polymerase and/or reverse transcriptase, 4 kinds of deoxyribonucleotide triphosphate, a reaction buffer, a labeled oligonucleotide probe, and a marker detection system.

The present invention is explained by illustrating figures.

FIGS. 3A–3E typically show the principle of the present invention, wherein 1 is a specific nucleic acid sequence and 2 is an oligonucleotide. The oligonucleotide has a base sequence A homologous to a part of the specific nucleic acid sequence (5' terminal side) and a base sequence B complementary to a part of the specific nucleic acid sequence (3' terminal side), and a spacer between the base sequence A and the base sequence B.

Procedure (a):

Oligonucleotide is annealed with a specific nucleic acid sequence.

When the specific nucleic acid sequence is double-stranded, it is denatured by alkali treatment, acid treatment, etc. into a single-stranded sequence. Heat denaturation is conducted by, for example, treatment at a temperature between 80° C. and 105° C. for 1 to 5 minutes. Alkali treatment is conducted by, for example, treatment in the presence of 0.2–1N sodium hydroxide for 1 to 30 minutes, followed by neutralization by an equivalent amount of hydrochloric acid. Acid treatment can be conducted by, for example, treatment in the presence of 0.01–1N hydrochloric acid for 1 to 30 minutes, followed by neutralization by sodium hydroxide. Other methods include enzymatic chain decomposition.

Annealing is carried out at a temperature selected so that the annealing selectivity is maximized with respect to the oligonucleotide. Usually, annealing is carried out at an increased temperature so that the specific nucleic acid and the oligonucleotide bind specifically and nonspecific binding by mismatch is minimized. The annealing temperature is normally about 30° to 70° C., although with no specific limitation.

Procedure (b):

Using the above-mentioned oligonucleotide as a primer, nucleic acid is synthesized with the use of nucleic acid polymerase.

This procedure is carried out by adding deoxyribonucleotide (e.g. dATP, dCTP, dGTP, dTTP) and DNA polymerase (e.g. *E. coli* DNA 1A polymerase, Klenow fragment, T4 DNA polymerase, T7 DNA polymerase, *Thermus aquaticus* DNA polymerase, *Thermus thermophilus* DNA polymerase) or reverse transcriptase and carrying out the elongation reaction using the specific nucleic acid as the template. This method is described in, for example, the Journal of Molecular Biology, 56, 341–361 (1971).

Procedure (c):

The oligonucleotide, which did not react in said elongation reaction, is decomposed, except for at least one part of the base sequence A homologous to a part of the specific nucleic acid sequence. This procedure can be carried out with the use of a nuclease, such as exonuclease III and Bal31 nuclease or a restriction enzyme. While the remaining base sequence is preferably identical with the base sequence A homologous to a part of the specific nucleic acid sequence, the sequence is only needed to have a sequence embraced in the sequence A.

When necessary, a method wherein the base sequence A homologous to a part of the specific nucleic acid sequence of the oligonucleotide is prepared into a phosphorothioate oligonucleotide, or a method wherein an oligonucleotide having a base sequence complementary to the base sequences A and B is added to the oligonucleotide to yield a double-stranded sequence may be employed as an auxiliary means.

Procedure (d):

The elongation product obtained in (b) is denatured into a single strand. Denaturation can be carried out by a method similar to the denaturation of the aforementioned specific nucleic acid sequence, with preference given to heat denaturation.

Procedure (e):

Using the single-stranded elongation product obtained in (d) as the template and the oligonucleotide obtained in (c) as the primer, nucleic acid is synthesized.

In the present invention, one nucleic acid can be amplified into two by carrying out the procedures (a) to (e).

In the present invention, procedure (f) or (f') is conducted in addition to (a) to (e).

Procedure (f):

The elongation product obtained in (e) is denatured into a single strand. Using the oligonucleotide obtained in (c) as the primer, an elongation product is repeatedly synthesized.

Procedure (f'):

The elongation product obtained in (e) is subjected to procedures (a) to (e) at least once, by which procedure, the specific nucleic acid sequence can be easily obtained in a larger amount.

In the present invention, procedure (g) is conducted in addition to (a) to (f).

Procedure (g):

The amplification product obtained in (f) is subjected to the procedures (a) to (e) or (a) to (f) described above at least once.

That is, by subjecting the product of procedure (e) and/or the amplification product obtained by repeating procedure (f), to one or more cycles of the procedures (a) to (e) or (a) to (f) as a sample nucleic acid, the amplification product can be obtained in larger amounts. When repeating the procedures, an oligonucleotide different from the one used in the first cycle of procedure (a) may be employed to give an amplification product of the specific nucleic acid sequence, which has a higher specificity.

In the nucleic acid amplification method of the present invention, by having at least a base sequence A homologous to a part of the specific nucleic acid sequence and a base sequence B complementary to the sequence at the 3' downstream position from said part of the specific nucleic acid sequence in sequential order from the 5' terminal to the 3' terminal, said base sequence B of the oligonucleotide is annealed with the specific nucleic acid sequence in the sample, followed by elongation reaction. Then, a base sequence A', which is complementary to the base sequence A of the specific nucleic acid is formed. Thereafter, the unreactive oligonucleotide is decomposed, except for at least a part of the base sequence A homologous to a part of the specific nucleic acid sequence, and used as a primer, which is annealed with the base sequence A' in the elongation product. Thus, the elongation reaction is repeated to amplify the sequence. In this method, nonspecific reaction is inhibited, since only one oligonucleotide is mixed with a sample and reacted. In addition, a high S/N (signal/noise) ratio can be obtained, since a mishybridization during procedure (a) and/or procedure (e) does not result in marked amplification of nonspecific substances, which is attributable to the use of only one oligonucleotide obtained in procedure (c) as the primer during the procedures (a) to (e), which are to be conducted in cycles. Also, the nucleic acid amplification method of the present invention is devoid of amplification of a probe derived from mismatch or nonspecific hybridization, when compared with the conventional amplification methods using probe, and is able to increase the S/N ratio.

As a result of the intensive study done by the present inventors, there has been also found that the conventional problems can be solved by using a first oligonucleotide complementary to at least a part of the specific nucleic acid sequence in a sample, and a second oligonucleotide having a base sequence B complementary to another part of the specific nucleic acid, and a base sequence A complementary to the first oligonucleotide in sequential arrangement in the direction from the 5' terminal to the 3' terminal.

Accordingly, the present invention essentially comprises the following procedures (a) to (e):

(a) A first oligonucleotide complementary to a part of the specific nucleic acid sequence, and a second oligonucleotide having a base sequence B complementary to another part of the specific nucleic acid and a base sequence A complementary to said first oligonucleotide in sequential arrangement in the direction from the 5' terminal to the 3' terminal are mixed with a sample for reaction, and said first oligonucleotide and said second oligonucleotide are annealed with the specific nucleic acid sequence in the sample.

(b) Using the annealed first oligonucleotide obtained in (a) as a primer, the nucleotide is elongated up to the 5' terminal of the annealed second oligonucleotide.

(c) The 3' terminal of the polynucleotide elongated in (b) is ligated to the 5' terminal of the annealed second oligonucleotide.

(d) The ligation product from (c) is separated from the template into a single strand.

(e) Using the single strand obtained in (d) as the template, the first oligonucleotide is reacted as the primer to yield an elongation product of the target nucleotide.

The embodiment of the present invention includes the following.

(1) A method for amplifying at least one specific nucleic acid sequence contained in a sample, which comprises the following procedures.

(a) A first oligonucleotide complementary to a part of the specific nucleic acid sequence, and a second oligonucleotide having a base sequence B complementary to another part of the specific nucleic acid and a base sequence A complementary to said first oligonucleotide in sequential arrangement in the direction from the 5' terminal to the 3' terminal are mixed with a sample for reaction, and said first oligonucleotide and said second oligonucleotide are annealed with the specific nucleic acid sequence in the sample.

(b) Using the annealed first oligonucleotide obtained in (a) as a primer, the nucleotide is elongated up to the 5' terminal of the annealed second oligonucleotide.

(c) The 3' terminal of the polynucleotide elongated in (b) is ligated to the 5' terminal of the annealed second oligonucleotide.

(d) The ligation product from (c) is separated from the template into a single strand.

(e) Using the single strand obtained in (d) as the template, the first oligonucleotide is reacted as the primer to yield an elongation product of the nucleotide.

(2) A method for amplifying at least one specific nucleic acid sequence contained in a sample, which comprises the following procedures.

(a) A first oligonucleotide complementary to a part of the specific nucleic acid sequence, and a second oligonucleotide having a base sequence B complementary to another part of the specific nucleic acid and a base sequence A complementary to said first oligonucleotide in sequential arrangement in the direction from the 5' terminal to the 3' terminal are mixed with a sample for reaction, and said first oligonucleotide and said second oligonucleotide are annealed with the specific nucleic acid sequence in a sample.

(b) Using the annealed first oligonucleotide obtained in (a) as a primer, the nucleotide is elongated up to the 5' terminal of the annealed second oligonucleotide.

(c) The 3' terminal of the polynucleotide elongated in (b) is ligated to the 5' terminal of the annealed second oligonucleotide.

(d) The ligation product from (c) is separated from the template into a single strand.

(e) Using the single strand obtained in (d) as the template, the first oligonucleotide is reacted as the primer to yield an elongation, product of the nucleotide.

(f) The amplification product obtained in (e) is subjected to one or more cycles of the procedures of separation from the template in (d) and synthesis of the nucleotide elongation product using the single strand from (e) as the template and the first oligonucleotide as the primer.

(3) A method for amplifying at least one specific nucleic acid sequence contained in a sample, which comprises the following procedures.

(a) A first oligonucleotide complementary to a part of the specific nucleic acid sequence, and a second oligonucleotide having a base sequence B complementary to another part of the specific nucleic acid sequence and a base sequence A complementary to the first oligonucleotide in sequential arrangement in the direction from the 5' terminal to the 3' terminal are mixed with a sample for reaction, and said first oligonucleotide and said second oligonucleotide are annealed with the specific nucleic acid sequence in the sample.

(b) Using the annealed first oligonucleotide obtained in (a) as a primer, the nucleotide is elongated up to the 5' terminal of the annealed second oligonucleotide.

(e) The 3' terminal of the polynucleotide elongated in (b) is ligated to the 5' terminal of the annealed second oligonucleotide.

(d) The ligation product from (c) is separated from the template into a single strand.

(e) Using the single strand obtained in (d) as the template, the first oligonucleotide is reacted as the primer to yield an elongation product of the nucleotide.

(f') The amplification product obtained in (e) is subjected to the procedures (a) to (e) at least once.

(4) A method for amplifying at least one specific nucleic acid sequence contained in a sample, which comprises the following procedures.

(a) A first oligonucleotide complementary to a part of the specific nucleic acid sequence, and a second oligonucleotide having a base sequence B complementary to another part of the specific nucleic acid and a base sequence A complementary to the first oligonucleotide in sequential arrangement in the direction from the 5' terminal to the 3' terminal are mixed with a sample for reaction, and said first oligonucleotide and said second oligonucleotide are annealed with the specific nucleic acid sequence in the sample.

(b) Using the annealed first oligonucleotide obtained in (a) as a primer, the nucleotide is elongated up to the 5' terminal of the annealed second oligonucleotide.

(c) The 3' terminal of the polynucleotide elongated in (b) is ligated to the 5' terminal of the annealed second oligonucleotide.

(d) The ligation product from (c) is separated from the template into a single strand.

(e) Using the single strand obtained in (d) as the template, the first oligonucleotide is reacted as the primer to yield an elongation product of the nucleotide.

(f) The amplification product obtained in (e) is subjected to one or more cycles of the procedures of separation from the template in (d) and synthesis of the nucleotide elongation product with the single strand from (e) as the template and the first oligonucleotide as the primer.

(g) The amplification product obtained in (f) is subjected to the procedures (a) to (e) or (a) to (f), at least once.

In the present invention, the first oligonucleotide and/or the second oligonucleotide to be used in procedure (f') may be different from the first oligonucleotide and/or the second oligonucleotide to be used in procedure (a) in the first cycle.

Also, the first oligonucleotide and/or the second oligonucleotide to be used in procedure (g) may be different from the first oligonucleotide and/or the second oligonucleotide to be used in procedure (a) in the first cycle.

Figure 4:
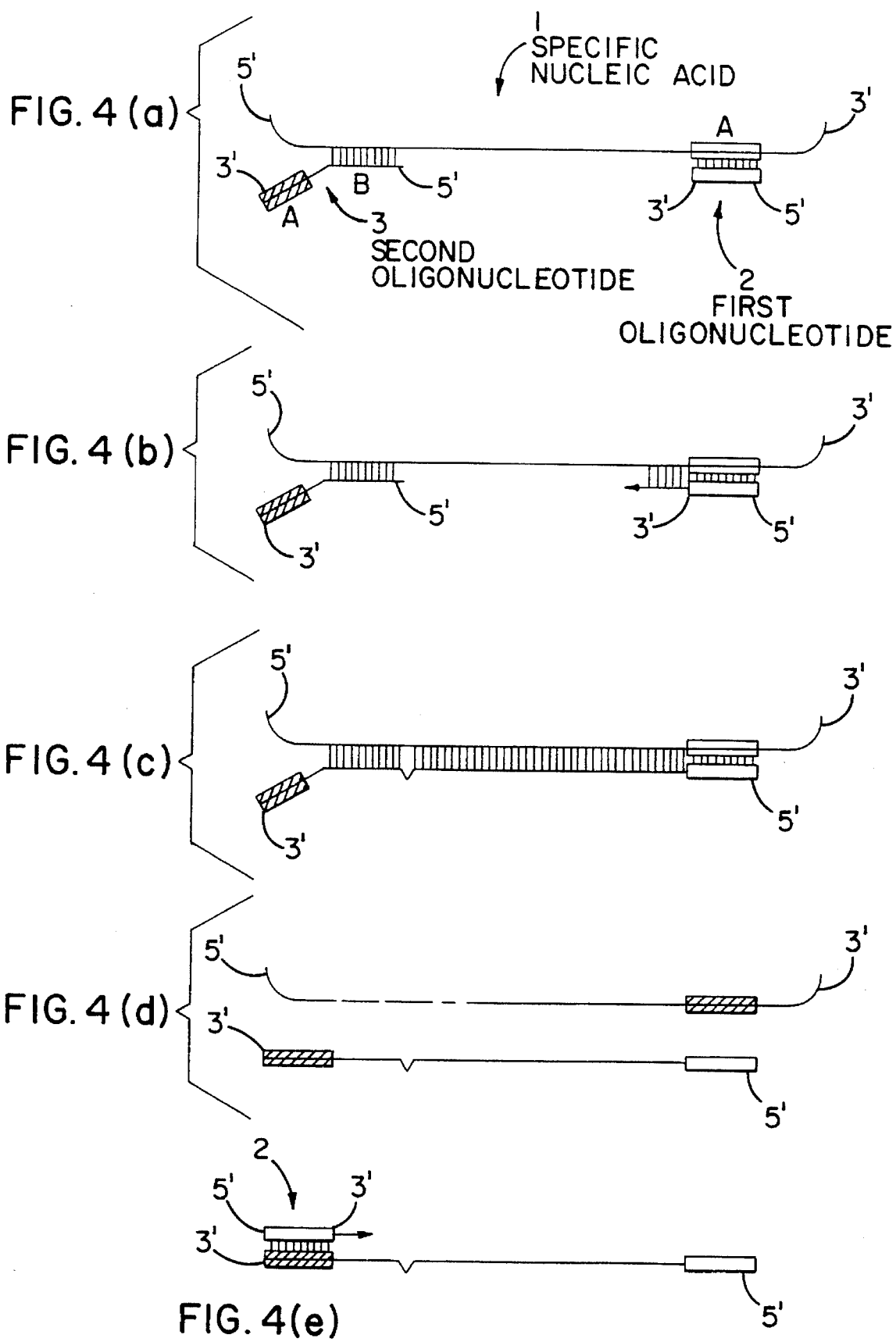
FIGS. 4A–4E schematically show the principle of the present invention, in which 1 is the specific nucleic acid, 2 is the first oligonucleotide, and 3 is the second oligonucleotide.

The first oligonucleotide of the present invention is only needed to have a base sequence complementary to a part of the specific nucleic acid sequence in a sample, and the structure and length thereof are not particularly limited (see FIG. 4, 2). Generally, the length thereof is 6–100 nucleotides, preferably 10–30 nucleotides.

Figure 3:
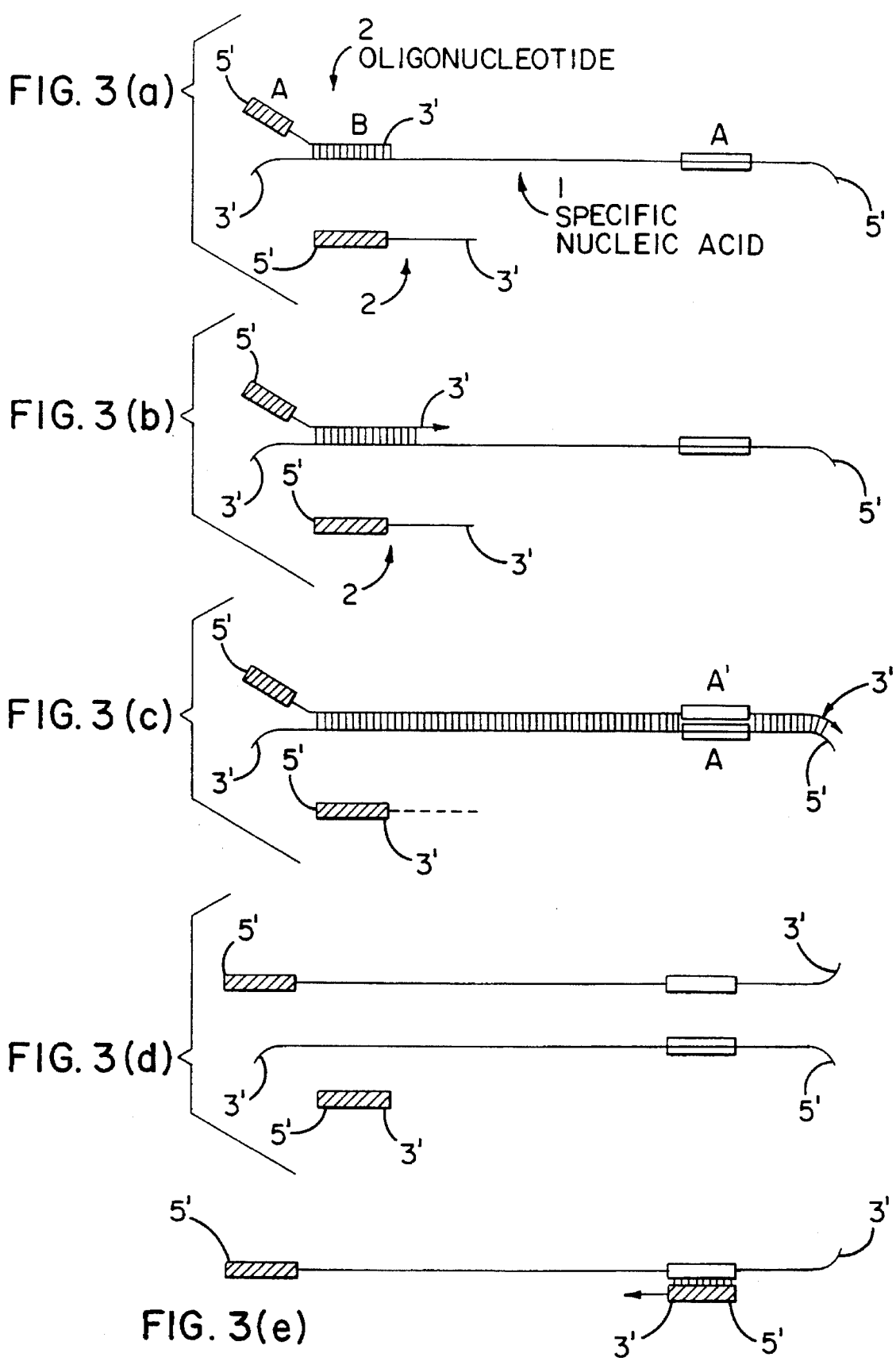
FIGS. 3A–3E schematically show the principle of the present invention, wherein 1 is the specific nucleic acid and 2 is the oligonucleotide.

The second oligonucleotide of the present invention has a base sequence B complementary to another part of the specific nucleic acid and a base sequence A complementary to the first oligonucleotide in sequential arrangement from the 5' terminal to the 3' terminal (see FIGS. 4A, 3). The first and the second oligonucleotides are selected so that the part complementary to the first oligonucleotide, which is a part of the specific nucleic acid, may be present at the site closer to the 3' terminal side than the part complementary to the second oligonucleotide, which is another part of the specific nucleic acid. No limitation is imposed on the structure and length thereof, except that the 3' terminal of the second oligonucleotide is designed to ligate to the 5' terminal of the elongation product, upon elongation of the first oligonucleotide. Generally, the length of the base sequence complementary to another part of the specific nucleic acid is 6–100 nucleotides, preferably 10–30 nucleotides.

With respect to the second oligonucleotide of the present invention, it is also possible to provide a spacer between the base sequence B complementary to another part of the specific nucleic acid and a base sequence A homologous to the first oligonucleotide. This spacer is generally 1–100, preferably 1–20 nucleotides in length. Said oligonucleotide can be synthesized by the phosphoamidite method, using a DNA synthesizer, such as the DNA synthesizer Model 391 (Applied Biosystems Inc.), and can be also synthesized by any other method, such as the phosphotriester method, the H-phosphonate method, the thiophosphite method, and so on. Also, they may be isolated from a biological origin and are exemplified by a restriction endonuclease digestion product.

A phosphate group is preferably bound to the 5' terminal of the second oligonucleotide. Binding of the phosphate group can be conducted using T4 polynucleotide kinase in the presence of ATP.

The reagent kit for the amplification of the target nucleic acid sequence of the present invention contains the first oligonucleotide and/or the second oligonucleotide, ligase, nucleic acid polymerase and/or reverse transcriptase, 4 kinds of deoxyribonucleotide triphosphate, and a reaction buffer.

The method for detecting the nucleic acid sequence of the present invention comprises the above-mentioned procedures (a), (b), (c), (d) and (e) or (a), (b), (c), (d), (e) and (f), or (a), (b), (c), (d), (e) and (f'), using a labeled first oligonucleotide and/or a labeled second oligonucleotide, and measuring said labeled marker for the detection of the target nucleic acid sequence.

Further, the method for detecting the nucleic acid sequence of the present invention comprises the above-mentioned procedures (a), (b), (c), (d) and (e) or (a), (b), (c), (d), (e) and (f), or (a), (b), (c), (d), (e) and (f'), adding a labeled oligonucleotide probe capable of hybridizing with the sequence to be detected in the product and/or its variant, and detecting the presence or absence of the hybridization for the detection of the target nucleic acid sequence.

The reagent kit for the detection of the target nucleic acid of the present invention contains the labeled first oligonucleotide and/or the labeled second oligonucleotide, ligase, nucleic acid polymerase and/or reverse transcriptase, 4 kinds of deoxyribonucleotide triphosphate, a reaction buffer, and a marker detection system.

Further, the reagent kit for the detection of the target nucleic acid sequence of the present invention contains the aforementioned first oligonucleotide and/or the second oligonucleotide, ligase, nucleic acid polymerase and/or reverse transcriptase, 4 kinds of deoxyribonucleotide triphosphate, a reaction buffer, a labeled oligonucleotide probe, and a labeled marker detection system.

The present invention is shown in FIGS. 4A–4E, based on which the present invention is described in the following. In the Figures, 1 stands for a specific nucleic acid sequence, 2 stands for a first oligonucleotide and 3 stands for a second oligonucleotide.

Procedure (a):

A first oligonucleotide and a second oligonucleotide are annealed with a specific nucleic acid sequence simultaneously or separately. In the present invention, the second oligonucleotide needs to be designed to anneal with the sequence at the 3' downstream position from the first oligonucleotide.

When the specific nucleic acid sequence is double-stranded, it is denatured by alkali treatment, acid treatment, etc. into a single-stranded sequence. Heat denaturation is conducted by, for example, treatment at a temperature between 80° C. and 105° C. for 1 to 5 minutes. Alkali treatment is conducted by, for example, treatment in the presence of 0.2–1N NaOH for 1 to 30 minutes, followed by neutralization with an equivalent amount of HCl. Acid treatment can be conducted by, for example, treatment in the presence of 0.01–1N HCl for 1 to 30 minutes, followed by neutralization with NaOH. Other methods include enzymatic chain decomposition.

Annealing is carried out at a temperature selected so that the annealing selectivity is maximized with respect to the first and the second oligonucleotides. Usually, annealing is carried out at an increased temperature so that the target nucleic acid sequence and the first and the second oligonucleotides bind specifically and nonspecific binding by mismatch is minimized. Annealing temperature is normally about 30° to 70° C., although with no specific limitation.

Procedure (b):

Using the above-mentioned first oligonucleotide as the primer, nucleic acid is synthesized with the use of nucleic acid polymerase. This procedure is carried out by adding deoxyribonucleotide (e.g. dATP, dCTP, dGTP, dTTP) and DNA polymerase (e.g. *E. coli* DNA 1A polymerase, Klenow fragment, T4 DNA polymerase, T7 DNA polymerase, *Thermus aquaticus* DNA polymerase, *Thermus thermophilus* DNA polymerase) or reverse transcriptase and carrying out the elongation reaction using the specific nucleic acid as the template. This method is described in, for example, the Journal of Molecular Biology, 56, 341–361 (1971).

Procedure (c):

The elongated sequence, which has proceeded to the 5' terminal of the second oligonucleotide annealed in (a), is ligated to the second oligonucleotide. It is preferable to use a ligase, such as T4 DNA ligase, T7 DNA ligase, E. coli DNA ligase, or Termus thermophilus DNA ligase, to ligate them.

Procedure (d):

The elongation-ligation product obtained in (c) is denatured into a single strand. Denaturation can be carried out by a method similar to the denaturation of the aforementioned specific nucleic acid sequence, with preference given to heat denaturation.

Procedure (e):

Using the single stranded elongation-ligation product obtained above as the template and the first oligonucleotide as the primer, nucleic acid is synthesized.

In the present invention, the specific nucleic acid sequence can be easily obtained in large amounts by repeating the yield of a single strand in (d) and nucleic acid synthesis using the first oligonucleotide as the primer in (e).

Further, by carrying out the procedure (a) and the following procedures with respect to the product of (e) and/or the amplification product obtained by repeating (d) and (e) as the sample nucleic acid, amplification product can be obtained in larger amounts.

In the present application, the first oligonucleotide and/or the second oligonucleotide to be used in procedure (f) may be different from the first oligonucleotide and/or the second oligonucleotide to be used in procedure (a) in the first cycle. Also, the first oligonucleotide and/or the second oligonucleotide to be used in procedure (g) may be different from the first oligonucleotide and/or the second oligonucleotide to be used in procedure (a) in the first cycle. By replacing the first and/or the second oligonucleotide(s) in (e) with different oligonucleotide(s), the amplification product of the specific nucleic acid, having higher specificity, can be obtained.

According to the amplification method of the present invention, amplification reaction occurs only when the first oligonucleotide, which has been annealed with the specific nucleic acid sequence and elongated, is ligated with the second oligonucleotide. Therefore, the specificity induced by the base sequence of oligonucleotide and the specificity in the conditions in which the elongation product and oligonucleotide are ligated are required, by which nonspecific reaction is more inhibited.

In addition, a high S/N (signal/noise) ratio can be obtained, since even if a mishybridization occurred, it does not result in marked amplification of nonspecific substances, which is attributable to the use of only one oligonucleotide as the primer during the procedures (d) and (e), which are to be carried out in cycles. Elongation and ligation can proceed with the use of heat-resistant DNA polymerase and heat-resistant DNA ligase and by varying the temperature of the reaction mixture, which allows easy amplification. The present amplification method causes no amplification of the probe remaining due to mismatch or nonspecific hybridization, when compared with the conventional amplification methods using probe, and is able to increase the S/N ratio.

The present invention is described in detail in the following examples to further clarify the effects of the present invention.

Reference Example 1

Synthesis of various oligonucleotides

Various oligonucleotides, having the following sequences, were synthesized by the phosphoamidite method, using the DNA synthesizer Model 391 (Applied Biosystems Inc.).

1) First oligonucleotide

This oligonucleotide comprises a sequence complementary to the nucleotide sequence 483–504 of Vibrio parahaemolyticus thermostable direct hemolysin, spacer and a sequence homologous to the nucleotide sequence 52–74 of Vibrio parahaemolyticus thermostable direct hemolysin (Sequence listing 1).

2) Second oligonucleotide

This oligonucleotide has a sequence complementary to the first oligonucleotide sequence 19–50 (Sequence listing 2), and is bound with an amino group at the 3' terminal.

3) Third oligonucleotide

This oligonucleotide is an oligonucleotide probe (24 mer), having a sequence complementary to the nucleotide sequence 103–126 of Vibrio parahaemolyticus thermostable direct hemolysin, and the phosphate group at the 5' terminal is labeled with $^{32}P$ as necessary (Sequence listing 3).

These oligonucleotides were synthesized at a 0.2 µM scale, according to the manual supplied by Applied Biosystems Inc. The various oligonucleotides were deprotected in aqueous ammonia at 55° C. overnight. Purification was carried out through a reversed-phase column, using FPLC produced by Pharmacia.

EXAMPLE 1

Amplification of specific nucleic acid

Procedure (a)

The first oligonucleotide (40 pmol) of Reference Example 1, genomic nucleic acids (1 ng and 100 pg) separated and partially purified from cultured cells of TDH-producing Vibro parahaemolyticus were added to the reaction solution (50 µl). After keeping the solution at 94° C. for 5 minutes, 4 units of Tth DNA polymerase (Toyo Boseki Kabushiki Kaisha) were added thereto. The mixture was kept at 94° C. for 1 minute, and incubated at 60° C. for 2 minutes for annealing.

Reaction mixture 10 mM Tris-HCl (pH 8.9)

1.5 mM $MgCl_2$ 80 mM KCl

500 µg/ml BSA 0.1% Sodium cholate 0.1% Triton X-100

2 mM dATP, dGTP, dCTP, dTTP

Procedure (b)

Elongation was carried out by keeping the mixture at 75° C. for 1.5 minutes.

Procedure (c)

The temperature was lowered to 37° C., exonuclease III (340 units) was added, and the mixture was incubated for 5 minutes for decomposition of a part of the unreacted oligonucleotide from (b).

Procedure (d)

After incubation at 94° C. for 2 minutes, amplification was carried out at the following cycle conditions.

Denaturation 94° C. for 60 seconds

Annealing 60° C. for 120 seconds

Elongation 75° C. for 90 seconds

Frequency 30 cycles

Procedure (e)

Figure 5:
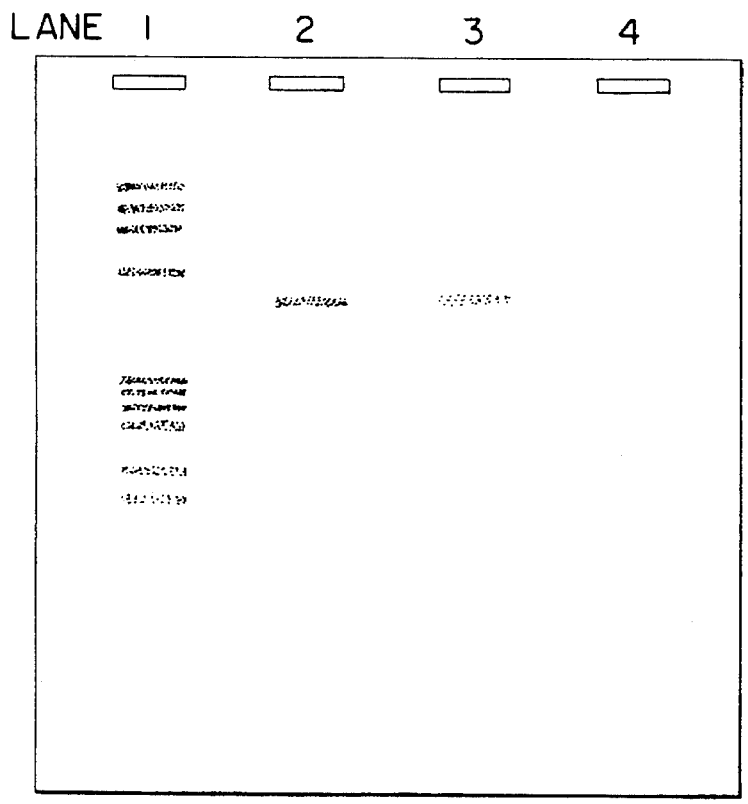
FIG. 5 shows electrophoresis patterns of the DNA synthesized in Example 1, in which lane 1 is a marker, 2, 3 and 4 respectively, correspond to 1 ng, 100 pg and 0 g of the nucleic acid sample of Example 2.

The amplification product was electrophoresed on agarose gel and subjected to ethidium bromide staining to find the synthesized DNA (FIG. 5). As a result, a band appeared near the position corresponding to 480 mer. This suggested that elongation of the first oligonucleotide and decomposition of the unreacted first oligonucleotide occurred, and a DNA was produced with a sequence homologous to a part of the specific nucleic acid sequence as the primer and the elongation product as the template.

EXAMPLE 2

Amplification of specific nucleic acid

Procedure (a)

The oligonucleotide (40 pmol) of Reference Example 1, genomic nucleic acids (1 ng and 100 pg) separated and partially purified from cultured cells of TDH-producing *Vibrio parahaemolyticus* were added to the reaction solution (50 µl). After keeping the solution at 94° C. for 5 minutes, 4 units of Tth DNA polymerase (Toyo Boseki Kabushiki Kaisha) were added thereto. The mixture was kept at 94° C. for 1 minute, and incubated at 60° C. for 2 minutes for annealing.

Reaction mixture 10 mM Tris-HCl (pH 8.9)
1.5 mM MgCl$_2$
80 mM KCl
500 µg/ml BSA
0.1% Sodium cholate
0.1% Triton X-100
2 mM dATP, dGTP, dCTP, dTTP Procedure (b)

Elongation was carried out by keeping the mixture at 75° C. for 1.5 minutes.

Procedure (c)

The second oligonucleotide (40 pmol) was added thereto, and the mixture was kept at 75° C. for 1 minute, after which it was incubated at 60° C. for 2 minutes for annealing with the unreacted first oligonucleotide.

Procedure (d)

The temperature was lowered to 37° C., exonuclease III (340 units) was added, and the mixture was incubated for 5 minutes for decomposition of a part of the unreacted oligonucleotide from (b).

Procedure (e)

After incubation at 94° C. for 2 minutes, amplification was carried out at the following cycle conditions.

Denaturation 94° C. for 60 seconds
Annealing 60° C. for 120 seconds
Elongation 75° for 90 seconds
Frequency 30 cycles Procedure (f)

Figure 6:
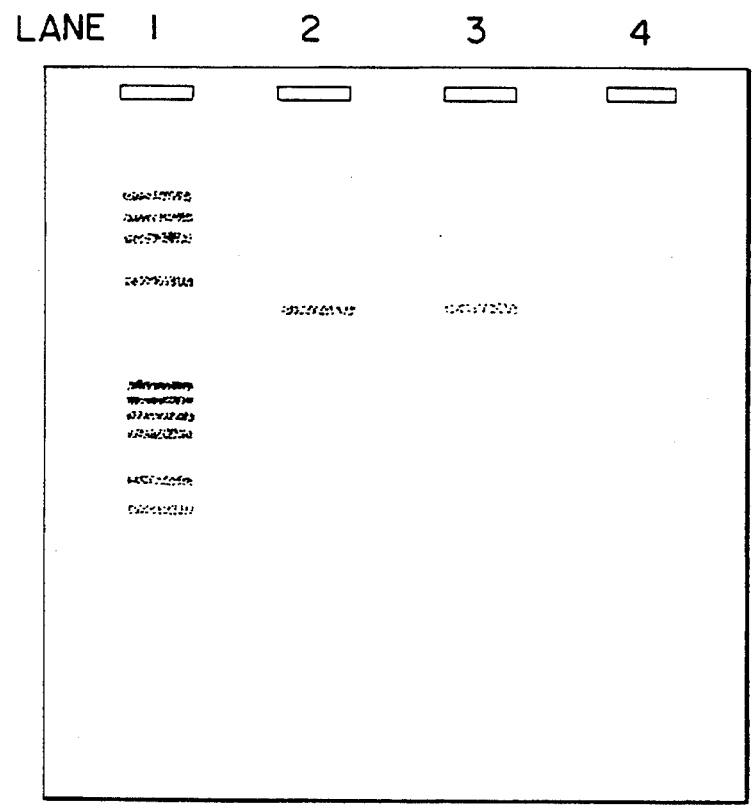
FIG. 6 shows electrophoresis patterns of the DNA synthesized in Example 2, in which lane 1 is a marker, 2, 3 and 4 respectively, correspond to 1 ng, 100 pg and 0 g of the nucleic acid sample of Example 2.

The amplification product was electrophoresed on agarose gel and subjected to ethidium bromide staining to find the synthesized DNA (FIG. 6). As a result, a band appeared near the position corresponding to 480 mer. This suggested that elongation of the first oligonucleotide and decomposition of unreacted first oligonucleotide, except a base sequence homologous to a part of the specific nucleic acid sequence which acted as the primer, occurred and a DNA was produced with the elongation product as the template.

EXAMPLE 3

Figure 7:
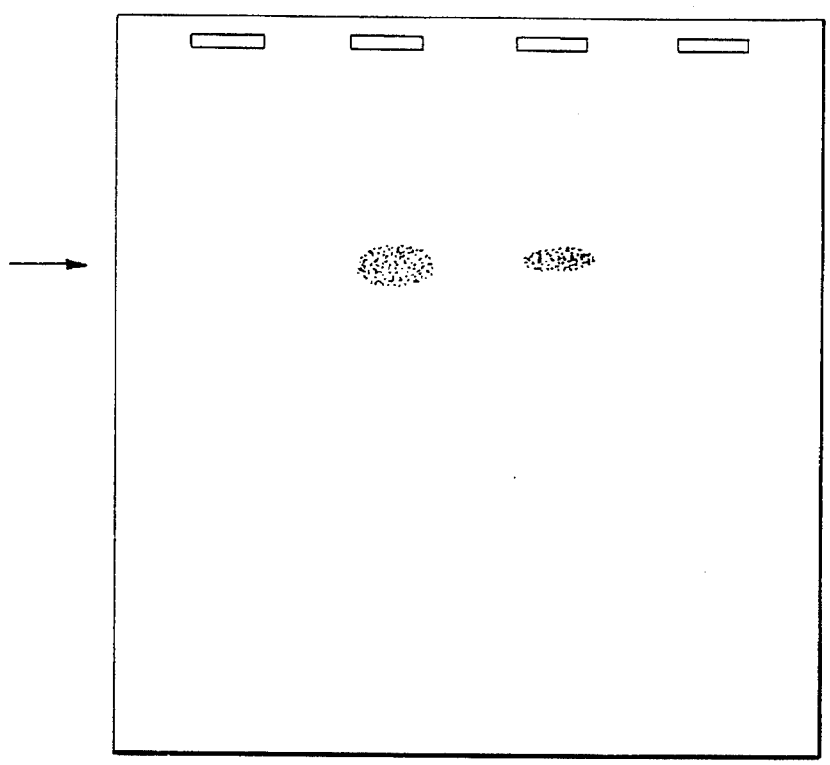
FIG. 7 shows sensitization patterns of the X-ray film sensitized in Example 3. The sensitized part corresponds to the DNA found by the ethidium bromide staining of Example 1.

The amplification product on the agarose gel obtained in (e) in Example 1 was transferred on a nylon membrane Hybond-n$^+$ (Amershem) by the Southern blot technique. The nylon membrane was prehybridized in 100 µl of a solution containing 6×SSC, 5×Denhard's solution, 1 mM EDTA and 10 µl of boiled salmon spermatic DNA (500 bases on average) at 60° C. for 1 hour. Then, a probe labeled with $^{32}$P at the 5' terminal phosphate group of the third oligonucleotide prepared in Reference Example 1 was added to the solution, and hybridization was carried out at 60° C. for 1 hour. After being thoroughly washed in 6×SSC at 60° C. and then dried, the nylon membrane was brought into contact with an X-ray film (New AIF RX, Fuji Photo Film Co., Ltd.) and exposed to light at −80° C. for one day and one night. As a result, the film was sensitized at the site corresponding to the DNA found by the ethidium bromide staining. This suggests that the DNA found by the ethidium bromide staining was a product exactly amplifying the target nucleic acid, and that a trace amount of the target nucleic acid was easily detected (FIG. 7).

Reference Example 2

Synthesis of various oligonucleotides

Various oligonucleotides, having the following sequences, were synthesized by the phosphoamidite method, using the DNA synthesizer Model 391 (Applied Biosystems Inc.).

1) First oligonucleotide

This oligonucleotide has a sequence complementary to the nucleotide sequence 483–504 of *Vibrio parahaemolyticus* thermostable direct hemolysin (Sequence listing 4).

2) Second oligonucleotide

This oligonucleotide has a sequence complementary to the nucleotide sequence 52–78 of *Vibrio parahaemolyticus* thermostable direct hemolysin, spacer and a sequence complementary to the first oligonucleotide (Sequence listing 5). A phosphate group is bound at the 5' terminal.

3) Third oligonucleotide

This oligonucleotide has a sequence complementary to the nucleotide sequence 400–421 of *Vibrio parahaemolyticus* thermostable direct hemolysin (Sequence listing 6).

4) Fourth oligonucleotide

This oligonucleotide has a sequence complementary to the nucleotide sequence 144–170 of *Vibrio parahaemolyticus* thermostable direct hemolysin, spacer and a sequence complementary to the third oligonucleotide (Sequence listing 7). A phosphate group is bound at the 5' terminal.

5) Fifth oligonucleotide

This oligonucleotide is an oligonucleotide probe having a sequence complementary to the nucleotide sequence 103–126 of *Vibrio parahaemolyticus* thermostable direct hemolysin, and the phosphate group at the 5' terminal is labeled with $^{32}$P as necessary (Sequence listing 8).

These oligonucleotides were synthesized at a 0.2 µM scale according to the manual supplied by Applied Biosystems Inc. The various oligonucleotides were deprotected in aqueous ammonia at 55°0 C. overnight. Purification was carried out through a reversed phase column using FPLC produced by Pharmacia. If necessary, the synthesized oligonucleotides were bound with a phosphoric acid at the 5' terminal by the following method.

oligonucleotide 5–20 pmoles
10×protruding end kinase buffer 10 µl
1 mM ATP 1 µl

T4 polynucleotide kinase (Toyo Boseki K. K.) 10 units

Water was added to make the total amount 100 μl, and the mixture was reacted at 37° C. for 1 hour. Here, 10×protruding end kinase buffer is as follows.

0.5M Tris-HCl (pH 8.0)
0.1M MgCl$_2$
0.1M 2-mercaptoethanol

EXAMPLE 4

Amplification of specific nucleic acid

Procedure (a)

The first oligonucleotide (40 pmol) and the second oligonucleotide (0.4 pmol) of Reference Example 2, genomic nucleic acids (1 ng and 100 pg) separated and partially purified from cultured cells of TDH-producing *Vibrio parahaemolyticus* were added to the reaction solution (20 μl). After keeping the solution at 94° C. for 5 minutes, it was incubated at 50° C. for 2 minutes for annealing.

Reaction mixture

10 Tris-HCl (pH 8.9)
1.5 mM MgCl$_2$
80 mM KCl
500 μg/ml BSA
0.1% Sodium cholate
0.1% Triton X-100
2 mM ATP, GTP, CTP, TTP
100 μM NAD Procedure (b)

Four units of Tth DNA polymerase (Toyo Boseki Kabushiki Kaisha), and 100 units of heat-stable DNA ligase (EPICENTRE TECHNOLOGIES) were added to the above-mentioned reaction mixture, and after keeping same at 65° C. for 2 minutes, it was incubated at 50° C. for 3 minutes for elongenation and ligation of oligonucleotide.

Procedure (e)

The elongation-ligation product obtained in (b) was used as the template, and the following amplification was carried out at the following cycle conditions.

Denaturation 94° C. for 60 seconds
Annealing 50° C. for 120 seconds
Elongation 75° C. for 90 seconds
Frequency 30 cycles Procedure (d)

Figure 8:
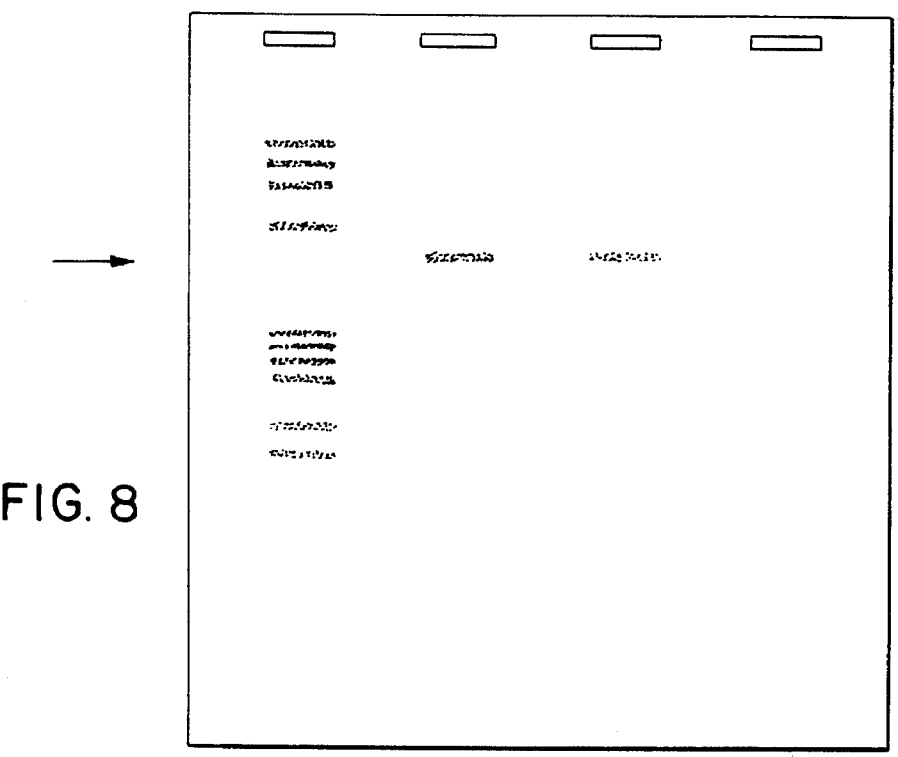
FIG. 8 shows the electrophoresis patterns of the DNA synthesized in Example 1 in which lane 1 is a marker, 2, 3 and 4 respectively, correspond to 1 ng, 100 pg and 0 g of the nucleic acid sample of Example 4.

The amplification product was electrophoresed on agarose gel and subjected to ethidium bromide staining to find the synthesized DNA (FIG. 8). As a result, a band appeared near the position corresponding to 480 mer. This suggested that elongation of the first oligonucleotide and ligation to the second oligonucleotide occurred and a DNA was produced with the elongation-ligation product as the template.

EXAMPLE 5

Amplification of specific nucleic acid from amplification product

Procedure (a)

The third oligonucleotide (40 pmol) and the fourth oligonucleotide (0.4 pmol) of Reference Example 1, and amplification product obtained in Example 1 which has been 100000-fold diluted (1 μl and 0.1 μl) were added to a reaction solution (20 μl). After keeping the solution at 94° C. for 5 minutes, it was incubated at 50° C. for 2 minutes for annealing.

Reaction mixture 10 mM Tris-HCl (pH 8.9)
1.5 mM MgCl$_2$
80 mM KCl
500 μg/ml BSA
0.1% Sodium cholate
0.1% Triton X-100
2 mM ATP, GTP, CTP, TTP
100 μM NAD Procedure (b)

Four units of Tth DNA polymerase (Toyo Boseki Kabushiki Kaisha), and 100 units of heat-stable DNA ligase (EPICENTRE TECHNOLOGIES) were added to the above-mentioned reaction mixture, and after keeping same at 65° C. for 2 minutes, it was incubated at 50° C. for 3 minutes for elongenation and ligation of oligonucleotide.

Procedure (c)

The elongation-ligation product obtained in (b) was used as the template, and the following amplification was carried out at the following cycle conditions.

Denaturation 94° C. for 60 seconds
Annealing 50° C. for 120 seconds
Elongation 75° C. for 90 seconds
Frequency 30 cycles Procedure (d)

Figure 9:
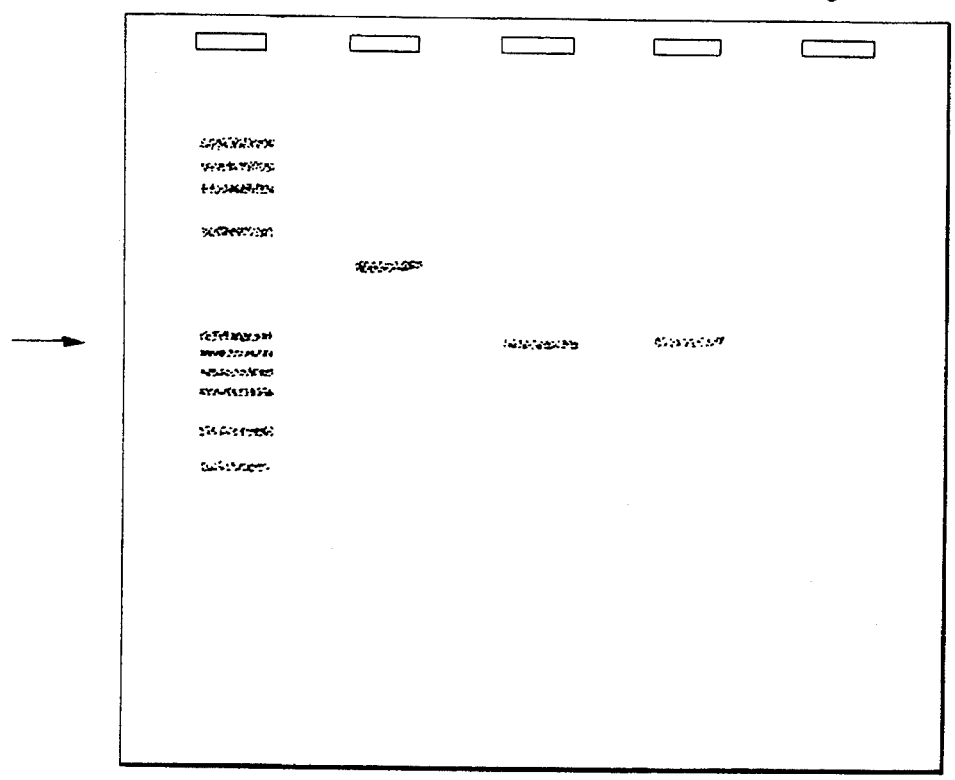
FIG. 9 shows the electrophoresis patterns of the DNA synthesized in Example 2, in which lane 1 is a marker, 2 is the amplification product of Example 4, and 3, 4 and 5, respectively, correspond to 1 μl, 0.1 μl and 0 μl of the nucleic acid sample of Example 5.

The amplification product was electrophoresed on agarose gel and subjected to ethidium bromide staining to find the synthesized DNA (FIG. 9). As a result, a band appeared near the position corresponding to 305 mer. This suggested that elongation of the third oligonucleotide, ligation thereof to the fourth oligonucleotide, and synthesis of the DNA with the elongation-ligation product as the template occurred.

EXAMPLE 6

Figure 10:
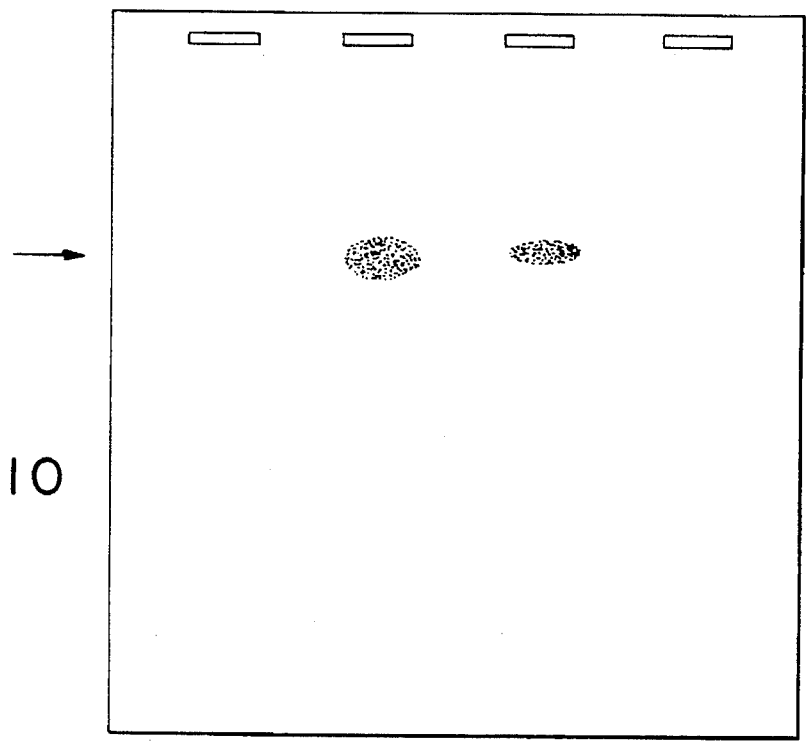
FIG. 10 shows sensitization patterns of the X-ray film sensitized in Example 6. The sensitized part corresponds to the DNA found by the ethidium bromide staining of Example 1.

The amplification product on the agarose gel obtained in (d) in Example 4 was transferred on a nylon membrane Hybond-n$^+$ (Amershem) by the Southern blot technique. The nylon membrane was prehybridized in 100 μl of a solution containing 6×SSC, 5×Denhard's solution, 1 mM EDTA and 10 μl of boiled salmon spermatic DNA (500 bases on average) at 60° C. for 1 hour. Then, the probe labeled with $^{32}$P at the 5' terminal phosphate group of the fifth oligonucleotide prepared in Reference Example 2 was added to the solution, and hybridization was carried out at 60° C. for 1 hour. After being thoroughly washed in 6×SSC at 60° C. and then dried, the nylon membrane was brought into contact with an X-ray film (New AIF RX, Fuji Photo Film Co., Ltd.) and exposed to light at −80° C. for one day and one night. As a result, the film was sensitized at the same site as the DNA found by the ethidium bromide staining. This suggests that the DNA found by the ethidium bromide staining was a product exactly amplifying the target nucleic acid, and that a trace amount of the target nucleic acid was easily detected (FIG. 10).

What is claimed is:

1. A method for amplifying at least one specific nucleic acid sequence contained in a sample, using initially as a primer an oligonucleotide having at least a base sequence A, which is 10–30 nucleotides in length and homologous to a part of a specific nucleic acid sequence to be amplified, and a base sequence B, which is 10–30 nucleotides in length and complementary to a sequence 3' to said part of the specific nucleic acid sequence to be amplified, wherein sequence A and sequence B are separated by a spacer region of 0–20 nucleotides and sequence A is located at the 5' end of said oligonucleotide and sequence B is located at the 3' end of said oligonucleotide, which comprises the following procedures:

(a) annealing sequence B of said oligonucleotide to the sequence 3' to said part of the specific nucleic acid sequence to be amplified in said sample to provide a first primer;

(b) elongating sequence B of the oligonucleotide, which was annealed to the sequence 3' to said part of the specific nucleic acid sequence to be amplified in the sample in (a);

(c) digesting from the 3' end of the oligonucleotide, which did not anneal to the specific nucleic acid sequence to be amplified in the sample in (a), with an exonuclease III, except for at least a part of the base sequence A, which will function as a second primer in (e);

(d) denaturing the elongation product obtained in (b) to a single strand; and (e) annealing sequence A of the oligonucleotide of (c) as a second primer to the single strand in (d), and elongating the sequence A of the oligonucleotide of (c) using the single strand obtained in (d) as a template.

2. A reagent kit for amplifying and, optionally, detecting a target nucleic acid comprising an oligonucleotide having at least a base sequence A, which is 10–30 nucleotides in length and homologous to a part of a specific nucleic acid sequence to be amplified, and a base sequence B, which is 10–30 nucleotides in length and complementary to a sequence 3' to said part of the specific nucleic acid sequence to be amplified, wherein sequence A and sequence B are separated by a spacer region of 0–20 nucleotides and sequence A is located at the 5' end of said oligonucleotide and sequence B is located at the 3' end of said oligonucleotide, sequence B functions as a first primer when hybridized to the sequence 3' to said part of the specific nucleic acid sequence to be amplified and sequence A, after elongation from the first primer and digestion from the 3' end of the oligonucleotide which did not anneal to the specific nucleic acid sequence to be amplified, except for at least a part of the base sequence A, and denaturation of the elongation product, functions as a second primer when hybridized to the denatured elongation product, an exonuclease III, an enzyme selected from the group consisting of nucleic acid polymerase, reverse transcriptase, and a combination of both, four kinds of deoxyribonucleotide triphosphates, and a reaction buffer.

3. A method for detecting a nucleic acid sequence in a sample, which comprises using initially as a primer an oligonucleotide having at least a base sequence A, of a specific nucleic acid sequence to be amplified, and a base sequence B, which is 10–30 nucleotides in length and complementary to a sequence 3' to said part of the specific nucleic acid sequence to be amplified, wherein sequence A and sequence B are separated by a spacer region of 0–20 nucleotides and sequence A is located at the 5' end of said oligonucleotide and sequence B is located at 3' end of said oligonucleotide, in the following procedures:

(a) annealing sequence B of said oligonucleotide to the sequence 3' to said part of the specific nucleic acid sequence to be amplified in said sample;

(b) elongating sequence B of the oligonucleotide which was annealed to the sequence 3' to said part of the specific nucleic acid sequence to be amplified in the sample in (a) as a first primer;

(c) digesting from the 3' end of the oligonucleotide which did not anneal to the specific nucleic acid sequence to be amplified in the sample in (a) with an exonuclease III except for at least a part of the base sequence A which will function as a primer in (e);

(d) denaturing the elongation product obtained in (b) to a single strand;

(e) annealing sequence A of the oligonucleotide of (c) as a second primer to the single strand obtained in (d), and elongating the sequence A of the oligonucleotide of (c) using the single strand obtained in (d) as a template; and (f) detecting the presence or absence of hybridization of an oligonucleotide probe which is complementary to the sequence which was elongated in (e) as an indication of the presence or absence, respectively, of at least one specific nucleic acid sequence in said sample.

4. The method of claim 1, which additionally comprises the following procedures:

(f) denaturing the elongation product obtained in (e) to a single strand;

(g) annealing sequence A of the oligonucleotide of (c) to the single strand obtained in (f);

(h) elongating the sequence A of the oligonucleotide of (c) using the single strand obtained in (f) as a template; and (i) generating an elongation product in at least one subsequent elongation reaction.

5. The method of claim 1, which additionally comprises the following procedure:

(f') repeating (a) through (e) at least once using the elongation product obtained in (e) as the specific nucleic acid sequence in (a).

6. The method of claim 4, which additionally comprises the following procedure:

(j) repeating (a) through (e) at least once using the elongation product obtained in (i) as the specific nucleic acid sequence in (a).

7. The method of claim 4, which additionally comprises the following procedure:

(j') repeating (a) through (i) at least once using the elongation product obtained in (i) as the specific nucleic acid sequence in (a).

8. The method of claim 5, wherein the oligonucleotide in (a) is different from the oligonucleotide in (f').

9. The method of claim 6, wherein the oligonucleotide in (a) is different from the oligonucleotide in (g).

10. The method of claim 7, wherein the oligonucleotide in (a) is different from the oligonucleotide in (g).

11. The method of claim 3, in which said sample is an elongation product.

12. The reagent kit of claim 2, in which said oligonucleotide is labeled with a label capable of being detected.

13. The method of claim 3, which comprises the following procedures (e'), (e") and (f') in place of (f):

(e') denaturing the elongation product obtained in (e) to a single strand;

(e") annealing sequence A of the oligonucleotide of (c) as a second primer to the single strand obtained in (e') as a template and elongating the sequence A of the nucleotide of (c) to generate an elongation product in at least one subsequent elongation reaction; and (f') detecting the presence or absence of hybridization of an oligonucleotide probe which is complementary to the sequence which was elongated in (e") as an indication of the presence or absence, respectively, of at least one specific nucleic acid sequence in said sample.

14. The method of claim 3, which comprises the following procedures (e'") and (f") in place of (f):

(e'") repeating (a) through (e) at least once using the elongation product obtained in (e) as the specific nucleic acid sequence in (a); and (f") detecting the presence or absence of hybridization of an oligonucleotide probe which is complementary to the sequence which was elongated in (e'") as an indication of the presence or absence, respectively, of at least one specific nucleic acid sequence in said sample.

15. The method of claim 3, in which said oligonucleotide probe contains a part of a base sequence of an oligonucleotide having at least a base sequence A, which is 10–30 nucleotides in length and homologous with a part of a specific nucleic acid sequence to be amplified, and a base sequence B, which is 10–30 nucleotides and complementary to a sequence 3' to said part of the specific nucleic acid sequence to be amplified, wherein sequence A and sequence B are separated by a spacer region of 0–20 nucleotides and sequence A is located at the 5' end of said oligonucleotide and sequence B is located at the 3' end of said oligonucleotide.

16. The method of claim 3, in which said oligonucleotide probe contains at least a base sequence A, which is 10–30 nucleotides in length and homologous with a part of a specific nucleic acid sequence to be amplified.

17. The method of claim 3, in which said oligonucleotide probe contains at least a base sequence B, which is 10–30 nucleotides in length and complementary to a sequence 3' to said part of the specific nucleic acid sequence to be amplified.

18. The method of claim 3, in which said oligonucleotide probe is labeled with a label capable of being detected.

* * * * *

UNITED STATES PATENT AND TRADEMARK OFFICE
CERTIFICATE OF CORRECTION

PATENT NO. : 5,525,462
DATED : June 11, 1996
INVENTOR(S) : Takarada et al.

It is certified that error appears in the above-indentified patent and that said Letters Patent is hereby corrected as shown below:

In Column 2, line 9: "target specific" should read --target-specific--.

In Column 2, line 38, 42, and 51: "4 respectively," should read --4, respectively,--.

In Column 2, line 49: "Example 1 in" should read --Example 1, in--.

In Column 3, line 57: "(f') in addition" should read --(f'), in addition--.

In Column 11, line 3: "*Termus*" should read --*Thermus*--.

In Column 12, line 7: "(Sequence listing 1)" should read --(SEQ ID NO:1)--.

In Column 12, line 10-11: "(Sequence listing 2)" should read --(SEQ ID NO:2).

In Column 12, line 17: "(Sequence listing 3)" should read --(SEQ ID NO: 3)--.

UNITED STATES PATENT AND TRADEMARK OFFICE
CERTIFICATE OF CORRECTION

PATENT NO. : 5,525,462
DATED : June 11, 1996
INVENTOR(S) : Takarada et al.

It is certified that error appears in the above-indentified patent and that said Letters Patent is hereby corrected as shown below:

In Column 14, lines 31, 36-37, 42, 46-47, and 54: "(Sequence listing 4); (Sequence listing 5); (Sequence listing 6); (Sequence listing 7); (Sequence listing 8)" respectively, should read --(SEQ ID NO:4); (SEQ ID NO:5); (SEQ ID NO:6); (SEQ ID NO:7); (SEQ ID NO:8)--.

In Column 15, line 22: "10 Tris-HCl" should read --10mM Tris-HCl--. In Column 15, line 38: "elongenation" should read --elongation--.

In Column 16, line 1: "100000-fold" should read --100,000-fold--.

In Column 16, line 22: "elongenation" should read --elongation--.

Signed and Sealed this

Eighteenth Day of March, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: other nucleic acid ( i x ) FEATURE:
( A ) NAME/KEY: misc_feature
( B ) LOCATION: 1..22
( D ) OTHER INFORMATION: complementary
sequence to the nucleotide sequence 483-504 of
Vibrio parahaemolyticus thermostable direct haemolysin ( i x ) FEATURE:
( A ) NAME/KEY: misc_feature
( B ) LOCATION: 23..27
( D ) OTHER INFORMATION: spacer ( i x ) FEATURE:
( A ) NAME/KEY: misc_feature
( B ) LOCATION: 27..50
( D ) OTHER INFORMATION: homologous
sequence to the nucleotide sequence 52-74 of
Vibrio parahaemolyticus thermostable direct haemolysin ( x i ) SEQUENCE DESCRIPTION: SEQ ID NO:1:

ACTACCACTC TCATATGCTT CTAAAAAGCT GCATTCAAAA CATCTGCTTT 50

( 2 ) INFORMATION FOR SEQ ID NO:2:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: other nucleic acid ( i x ) FEATURE:
( A ) NAME/KEY: misc_feature
( B ) LOCATION: 1..32
( D ) OTHER INFORMATION: complementary sequence to the nucleotide sequence 19-50 of the first oligonucleotide ( x i ) SEQUENCE DESCRIPTION: SEQ ID NO:2:

AAAGCAGATG TTTTGAATGC AGCTTTTTAG AA 32

( 2 ) INFORMATION FOR SEQ ID NO:3:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid ( i x ) FEATURE:
( A ) NAME/KEY: misc_feature
( B ) LOCATION: 1..24
( D ) OTHER INFORMATION: complementary sequence to the nucleotide sequence 103-126 of Vibrio parahaemolyticus thermostable direct haemolysin ( x i ) SEQUENCE DESCRIPTION: SEQ ID NO:3:

AAACAATATC TCATCAGAAC CGGG                                                24

( 2 ) INFORMATION FOR SEQ ID NO:4:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( i x ) FEATURE:
    ( A ) NAME/KEY: misc_feature
    ( B ) LOCATION: 1..22
    ( D ) OTHER INFORMATION: complementary
          sequence to the nucleotide sequence 483-504 of
          Vibrio parahaemolyticus thermostable direct haemolysin ( x i ) SEQUENCE DESCRIPTION: SEQ ID NO:4:

ACTACCACTC TCATATGCTT CT                                                  22

( 2 ) INFORMATION FOR SEQ ID NO:5:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: other nucleic acid ( i x ) FEATURE:
    ( A ) NAME/KEY: misc_feature
    ( B ) LOCATION: 1..27
    ( D ) OTHER INFORMATION: complementary
          sequence to the nucleotide sequence 52-78 of
          Vibrio parahaemolyticus thermostable direct haemolysin ( i x ) FEATURE:
    ( A ) NAME/KEY: misc_feature
    ( B ) LOCATION: 28..32
    ( D ) OTHER INFORMATION: spacer ( i x ) FEATURE:
    ( A ) NAME/KEY: misc_feature
    ( B ) LOCATION: 33..54
    ( D ) OTHER INFORMATION: complementary
          sequence to the oligonucleotide of SEQ ID NO:4

( x i ) SEQUENCE DESCRIPTION: SEQ ID NO:5:

CTCAAAAGCA GATGTTTTGA ATGCAGCAAA AAAGAAGCAT ATGAGAGTGG TAGT              54

( 2 ) INFORMATION FOR SEQ ID NO:6:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( i x ) FEATURE:
    ( A ) NAME/KEY: misc_feature
    ( B ) LOCATION: 1..22
    ( D ) OTHER INFORMATION: complementary
          sequence to the nucleotide sequence 400-421 of
          Vibrio parahaemolyticus thermostable direct haemolysin ( x i ) SEQUENCE DESCRIPTION: SEQ ID NO:6:

CTTCACCAAC AAAGTTAGCT AC                                                                          2 2

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: misc_feature
        ( B ) LOCATION: 1..27
        ( D ) OTHER INFORMATION: complementary
            sequence to the nucleotide sequence 144-170 of
            Vibrio parahaemolyticus thermostable direct haemolysin ( i x ) FEATURE:
        ( A ) NAME/KEY: misc_feature
        ( B ) LOCATION: 28..32
        ( D ) OTHER INFORMATION: spacer ( i x ) FEATURE:
        ( A ) NAME/KEY: misc_feature
        ( B ) LOCATION: 33..54
        ( D ) OTHER INFORMATION: complementary
            sequence to the oligonucleotide of SEQ ID NO:6

( x i ) SEQUENCE DESCRIPTION: SEQ ID NO:7:

ACATTGACCG GAGCTTGGGT ATTAAAAAAA AAGTAGCTAA CTTTGTTGGT GAAG                   5 4

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: misc_feature
        ( B ) LOCATION: 1..24
        ( D ) OTHER INFORMATION: complementary
            sequence to the nucleotide sequence 103-126 of
            Vibrio parahaemolyticus thermostable direct haemolysin ( x i ) SEQUENCE DESCRIPTION: SEQ ID NO:8:

AAACAATATC TCATCAGAAC CGGG                                                                        2 4